(12) United States Patent
Stuart et al.

(10) Patent No.: US 7,723,119 B2
(45) Date of Patent: May 25, 2010

(54) METHOD FOR DETERMINING SOLUBILITY OF A CHEMICAL COMPOUND

(75) Inventors: Martin Stuart, Haywards Heath (GB); Karl Julian Box, East Grinstead (GB)

(73) Assignee: Sirius Analytical Instruments Ltd., East Sussex (GB)

(*) Notice: Subject to any disclaimer, the term of this patent is extended or adjusted under 35 U.S.C. 154(b) by 685 days.

(21) Appl. No.: 11/597,640

(22) PCT Filed: May 11, 2005

(86) PCT No.: PCT/GB2005/001783

§ 371 (c)(1),
(2), (4) Date: Nov. 27, 2006

(87) PCT Pub. No.: WO2005/116635

PCT Pub. Date: Dec. 8, 2005

(65) Prior Publication Data

US 2007/0196929 A1    Aug. 23, 2007

(30) Foreign Application Priority Data

May 25, 2004    (GB)   ............................... 0411609.1

(51) Int. Cl.
*G01N 31/16* (2006.01)
*G01N 1/10* (2006.01)
(52) U.S. Cl. .................... 436/163; 436/166; 436/174; 436/179; 73/866
(58) Field of Classification Search ............... 436/163, 436/166, 174, 179; 73/866
See application file for complete search history.

(56) References Cited

U.S. PATENT DOCUMENTS 6,004,822 A    12/1999   Li et al.

FOREIGN PATENT DOCUMENTS

JP    11 221433 A    8/1999
WO    WO 01/55698 A    8/2001

OTHER PUBLICATIONS

Alex Avdeef, "pH-metric Solubility. 1. Solubility-pH Profiles from Bjerrum Plots. Gibbs Buffer and $pK_a$ in the Solid State," Pharm. Pharmacol. Commun. 1998, 4: pp. 165-178.

(Continued)

*Primary Examiner*—Jill Warden
*Assistant Examiner*—Timothy G Kingan
(74) *Attorney, Agent, or Firm*—Muncy, Geissler, Olds & Lowe, PLLC (57) ABSTRACT

There is provided a method of determining the solubility of a chemical compound containing one or more acidic or basic groups. The method involves preparing a close to saturated solution with solid present of said chemical compound; measuring the pH of the test solution at regular intervals until a consistent rate of pH change; adding a known aliquot of base or acid titrant to the test solution to adjust the pH slope; and repeating steps (b) and (c) until the measured pH slope changes sign. The solubility of the compound is determined as the concentration of unionised compound in solution when the measured pH slope is interpolated to zero.

14 Claims, 9 Drawing Sheets

OTHER PUBLICATIONS

Alex Avdeef et al., "pH-metric Solubility. 2: Correlation Between the Acid-Base Titration and the Saturation Shake-Flask Solubility-ph Methods," Pharmaceutical Research, vol. 17, No. 1, 2000, pp. 85-89.

T.J. Roseman et al., "Physicochemical Properties of Prostaglandin $F_{2\alpha}$ (Tromethamine Salt): Solubility Behavior, Surface Properties, and Ionization Constants," Journal of Pharmaceutical Sciences, 1973, vol. 62, No. 10; pp. 1680-1685.

William H. Streng et al., "General treatment of pH solubility profiles of weak acids and bases. II. Evaluation of thermodynamic parameters from the temperature dependence of solubility profiles applied to a zwitterionic compound," International Journal of Pharmaceutics, 1985, 25: pp. 135-145.

Streng W. H. et al., "General Treatment of PH Solubility Profiles of Weak Acids and Bases 2. Evaluation of Thermodynamic Parameters from the Temperature Dependence of Solubility Profiles Applied to a Zwitteronic Compound," International Journal of Pharmaceutics (Kidlington), vol. 25, No. 2, 1985, pp. 135-145; XP002344667; ISSN: 0378-5173; abstract, pp. 139-140.

METHOD FOR DETERMINING SOLUBILITY OF A CHEMICAL COMPOUND

This application is the national phase under 35 U.S.C. §371 of PCT International Application No. PCT/GB2005/001783, which has an International filing date of May 11, 2005, and designated the United States of America, which claims priority to GB 041 1609.1, which was filed on May 25, 2004, and which are all incorporated herein by reference.

TECHNICAL FIELD

The present invention relates to a method for determining the solubility of a chemical compound. In particular, the present invention relates to method for more rapid determination of the solubility of an organic chemical compound having one or more acidic or basic groups.

BACKGROUND TO THE INVENTION

The determination of the solubility of a chemical compound is a routine requirement in analytical chemistry laboratories. Such determination is for example, commonly required in the development and assessment of new pharmaceutical and agrochemical compounds, many of which contain one or more acidic or basic groups that react with hydrogen ions in aqueous solution.

Traditional methods of determining solubility rely on the addition of a known mass of chemical compound to a known volume of distilled water at a defined pH. The resulting solution is agitated (e.g. by stirring) until an equilibrium state is obtained. Samples of the equilibrated solution are then removed and the solubility determined by known analytical methods. A problem with such traditional methods is that it is not unusual for an extended period of time, sometimes in excess of 48 hours, to be required for an equilibrium state to be reached. Thus, the process is undesirably slow. In addition, over such an extended time period it is not uncommon for environmental factors to affect the test solution. For example, atmospheric carbon dioxide may dissolve in the solution to produce carbonic acid, thereby potentially affecting the pH thereof. Alternatively, the chemical compound itself may be subject to environmental degradation (e.g. as a result of oxidation by atmospheric oxygen).

Overall, it is therefore desirable both from an efficiency and accuracy standpoint to provide a method for more rapid determination of solubility.

A pH-metric method of determining solubility has been described in the literature: 'pH-metric Solubility. 1. Solubility-pH Profile from Bjerrum Plots. Gibbs Buffer and $pK_a$ in the Solid State: Pharm Pharmacol Commun 1998, 4: pages 165-178; and 'pH-metric Solubility. 2. Correlation Between the Acid-Base Titration and the Saturation Shake-Flask Solubility-pH Methods: Pharmaceutical Research, 2000, 17: pages 85-89. In practice, however this method still typically requires from six to eight hours to conduct and therefore represents only a partial advance over the traditional methods.

The Applicant has now developed a method of determining the solubility of chemical compounds containing one or more acidic or basic groups that is much faster than both traditional and pH-metric methods. A typical solubility determination can be conducted in less than an hour (e.g. 30 to 60 minutes), thereby providing significant process efficiency benefits and reducing the likelihood of environmental factors having any affect on the result. The method may be used for even poorly soluble chemical compounds and is readily susceptible to automation. Additionally, the method of the present invention does not necessarily require the use of co-solvents as are commonly used in more traditional methods, particularly when assessing compounds of low solubility.

Traditional methods of determining solubility are for example, described in the following literature references: The article 'Physiochemical Properties of Prostaglandin $F_{2\alpha}$ (Tromethamine Salt): Solubility Behavior, Surface Properties, and Ionization Constants: Journal of Pharmaceutical Sciences, 1973, 62: pages 1680-5 describes a method of solubility determination of the subject prostaglandin drug that requires 48 hours for equilibrium to be reached and in which, environmental degradation of the drug over 48 hours is noted at $pH \leq 3$. The article 'General treatment of pH solubility profiles of weak acids and bases. II. Evaluation of thermodynamic parameters from the temperature dependence of solubility profiles applied to a zwitterionic compound: International Journal of Pharmaceutics, 1985, 25: pages 135-145 describes a method of solubility determination that requires 3-5 days for an equilibrium state to be reached.

It is an object of the present invention to provide a method of determining the solubility of chemical compounds containing one or more acidic or basic groups that is more efficient than known methods.

It is an object of the present invention to provide a method of determining the solubility of pharmaceutical or agrochemical chemical compounds containing one or more acidic or basic groups that is more rapid than known methods.

SUMMARY OF THE INVENTION

According to a first aspect of the present invention there is provided a method of determining the solubility of a chemical compound containing one or more acidic or basic groups comprising (a) preparing a close to saturated solution of said chemical compound with solid of the chemical compound present;

(b) measuring the pH of the test solution at regular intervals until a consistent rate of pH change is obtained, and measuring the slope of said consistent rate of pH change;

(c) adding a known aliquot of base or acid titrant to the test solution to adjust the pH slope;

(d) repeating steps (b) and (c) until the measured pH slope changes sign;

(e) determining the solubility of the compound as the concentration of unionised compound in solution when the measured pH slope is interpolated to zero.

The first step of the method requires freshly preparing a close to saturated solution of said chemical compound with solid of the chemical compound present therein. By 'close to saturated solution' it is meant a solution that is close to its saturation point (at that pH), which may either be weakly sub-saturated or weakly super-saturated. It must be the solid of the chemical compound that is present rather than a salt thereof.

The close to saturated solution with solid present may be prepared by any suitable method. One suitable method for preparing the close to saturated solution with solid present involves the steps of (i) providing a known volume of water and a known amount of said compound to a titration vessel to form a test solution;

(ii) optionally, adding a volume of base or acid titrant to said test solution sufficient to adjust the pH thereof to fully dissolve the compound in ionised form, thereby creating a hyperconcentrated solution;

(iii) adding one or more known aliquots of acid or base titrant to the test solution until the unionised compound begins to precipitate out of the test solution;

(iv) optionally, adding one or more additional known aliquots of acid or base titrant to the test solution to cause additional precipitation of the unionised compound out of the test solution.

It will be appreciated that the nature of acid or base titrant added in step (c) of the method or steps (ii)-(iv) above is determined by whether the compound whose solubility is to be tested has either acidic or basic groups. In general terms, where the compound has acidic groups, base titrant is added to cause dissolution and acid titrant is added to cause precipitation. Where the compound has basic groups, acid titrant is added to cause dissolution and base titrant is added to cause precipitation.

Thus, a suitable method for preparing the close to saturated solution with solid present of a chemical compound containing one or more acidic groups involves the steps of (i) providing a known volume of water and a known amount of said compound to a titration vessel to form a test solution;

(ii) optionally, adding a volume of base titrant to said test solution sufficient to adjust the pH thereof to fully dissolve the compound in ionised form, thereby creating a hyperconcentrated solution;

(iii) adding one or more known aliquots of acid titrant to the test solution until the unionised compound begins to precipitate out of the test solution;

(iv) optionally, adding one or more additional known aliquots of acid titrant to the test solution to cause additional precipitation of the unionised compound out of the test solution.

A suitable method for preparing the close to saturated solution with solid present of a chemical compound containing one or more basic groups involves the steps of (i) providing a known volume of water and a known amount of said compound to a titration vessel to form a test solution;

(ii) optionally, adding a volume of acid titrant to said test solution sufficient to adjust the pH thereof to fully dissolve the compound in ionised form, thereby creating a hyperconcentrated solution;

(iii) adding one or more known aliquots of base titrant to the test solution until the unionised compound begins to precipitate out of the test solution;

(iv) optionally, adding one or more additional known aliquots of base titrant to the test solution to cause additional precipitation of the unionised compound out of the test solution.

The method herein is suitable for determining the solubility of a chemical compound containing one or more acidic or basic groups. In aspects, the chemical compound contains only basic groups; or contains only acidic groups; or contains both acidic and basic groups (e.g. a zwitterionic compound).

The method relies on there being (a) an available pH range where a significant proportion of the compound is ionised so as to allow dissolution to take place; and (b) there is an available pH range where a significant proportion of the compound is unionised and can precipitate.

Acidic and basic groups react with hydrogen ions in aqueous solution. Chemical compounds containing acidic or basic groups that react with hydrogen ions in aqueous solution are referred to herein as "ionisable solutes". The chemical compound can be introduced as a free acid or base or it may be introduced as a salt of the acid or base (e.g. sodium salt).

Many pharmaceutical and agrochemical compounds contain one or more acidic or basic groups such as carboxylic acids, phenols, amines or pyridines. The method herein is therefore particularly suitable for use in determining the solubility of such pharmaceutical compounds.

The method herein is suitable for determining the solubility of compounds with a wide range of solubilities, typically in the range from 100 ng/ml to 30 mg/ml. Co-solvent may be employed to widen the range of compounds for which solubility can be readily measured.

The method herein is also suitable for determining the solubility of chemical compounds of low solubility such as compounds having a solubility of less than 1 µg/ml.

The dissociation of an ionisable solute (e.g. a weak acid) AH in aqueous solution may be expressed as:

Wherein $AH_{aq}$ and $A^-_{aq}$ are referred to as "species".

The dissolution of a solid may be represented as:

A "saturated solution" of an ionisable solute is defined herein to be a solution of the solute which also contains the solute in undissolved form, and which is at equilibrium. A saturated solution contains the maximum concentration of the solute which will dissolve in that solution at a given temperature, ionic strength and pH background.

The term "intrinsic solubility" is defined herein as the concentration of the unionised species of an ionisable solute in a saturated solution of the solute. The intrinsic solubility of an ionisable solute is a constant for a given temperature and ionic strength background of an aqueous solution.

A "hyperconcentrated solution" is defined herein to be a solution of an ionisable solute that contains sufficient weight of solute such that, while the solute is fully dissolved at a pH where it is predominantly ionised, the unionised form of the solute will precipitate if the pH is adjusted to a pH where the solute is predominantly unionised.

A "supersaturated solution" is defined herein to be a hyperconcentrated solution in which the concentration of unionised species in solution is higher than the intrinsic solubility. Supersaturated solutions are not at equilibrium. Supersaturated solutions may be created by changing the pH of a solution of ionised solute by adding acidic or alkaline titrant rapidly from a pH at which the solute is ionised to a pH at which it is unionised. It takes time for a precipitate to form around nucleation sites in the solution and the concentration of unionised species in solution may therefore temporarily exceed the intrinsic solubility until the system has reached equilibrium.

A "subsaturated solution" is defined herein as a hyperconcentrated solution in which the concentration of unionised species is lower than the intrinsic solubility.

The method herein initially requires that a close to saturated solution with solid present of the chemical compound containing one or more acidic or basic groups (i.e. the ionisable solute) be prepared. In one aspect, a quantity of ionisable solute sufficient to form a hyperconcentrated solution is accurately weighed into a titration vessel. In another aspect, a measured volume of pre-prepared hyperconcentrated solution is accurately pipetted into the titration vessel. In both aspects, a measured volume (e.g. 10 mL) of water or of an aqueous solution of an inert electrolyte (e.g. 0.15M KCl) is then added to the titration vessel such that the test solution remains hyperconcentrated. Co-solvent (e.g. methanol, ethanol, acetone, methylethyl ketone or any other water-miscible organic solvent) is optionally added to the test solution. The volume and concentration of the so-prepared test solution is recorded.

To fully dissolve the compound in ionised form, the method may optionally, require adding a volume of base or acid titrant to said test solution sufficient to adjust the pH thereof for full dissolution of the compound. In particular, if the compound is introduced as a salt then the sample must be fully dissolved so that the amount of counter-ion introduced is known.

To cause precipitation, the method may then require adding one or more known aliquots of acid or base titrant to the test solution until the compound begins to precipitate out of the test solution. Precipitation is typically detected by a visual or spectroscopic method (i.e. as the test solution goes cloudy).

To ensure the presence of sufficient precipitate for efficient carrying out of the later stages of the method, the method may optionally, require adding one or more additional known aliquots of acid or base titrant to the test solution to cause additional precipitation of the compound out of the test solution.

Once the close to saturated solution with solid present of the chemical compound has been prepared, the method then involves measuring the pH of the test solution at regular intervals until a consistent rate of pH change is obtained, and measuring the slope of said consistent rate of pH change.

A known aliquot of base or acid titrant is then added to the test solution to adjust the pH slope. In effect, this step acts such as to bring the test solution to be more nearly in equilibrium with the precipitate.

The pH slope measurement and base or acid titrant steps are repeated until the measured pH slope changes sign. The solubility of the compound is determined as the concentration of unionised compound in solution when the measured pH slope is interpolated to zero. Such determination generally requires plotting a graph of concentration of unionised compound in solution (calculated by reference to known characteristics of the compound and test solution) against pH slope, and the use of interpolation to identify the zero pH slope value.

It is desirable to repeat the steps of the method at least once, preferably from 2 to 8 times, sufficient to give enough data points for the subsequent calculation stage.

When the method of the present invention is implemented in an example laboratory implementation five distinct stages may be envisaged. These stages are herein described as the Dissolution, Seeking Precipitation, Additional Precipitation, Chasing Equilibrium and Re-Dissolution stages. It will be appreciated that it is the Chasing Equilibrium stage that is at the core of the method of the present invention. Suitably, the pH of the solution is measured throughout the method and the test solution is mixed (e.g. by stirring) throughout the method. The rate of mixing may be varied at different stages of the method.

1. Dissolution Stage

A test solution is formed by providing a known volume of water and a known weight of said compound to a titration vessel. A measured volume of either acid or base titrant (e.g. standardised 0.1M HCl, 0.1M KOH) is added to the test solution to adjust it to a pH at which the ionisable solute is fully dissolved in its ionised form. If the ionisable solute is an acid, the pH is adjusted by adding base titrant. If the ionisable solute is a base, the pH is adjusted by adding acid titrant. The test solution should not be turbid after the pH has been adjusted. The volume of standardised acid or base added in the Dissolution stage is recorded.

2. Seeking Precipitation

This stage takes place after the pH has been adjusted in the Dissolution stage. The test solution is titrated by adding measured aliquots of base or acid titrant until the solution becomes cloudy, which indicates that the poorly soluble unionised species has precipitated. The volumes of titrant used are recorded. The volumes of aliquots added during this stage are calculated to achieve a fast titration without overshooting the precipitation point by more than about 1 pH unit.

The occurrence of precipitation may be observed by eye. However it is more convenient to detect the occurrence of precipitation using a spectroscopic dip probe connected to a spectrophotometer. A wavelength is chosen at which the solution of ionised solute absorbs little or no light at any pH where no precipitate is present. The first appearance of precipitate is detected by noting the sharp reduction in the amount of light transmitted at that wavelength, caused by the absorption and scattering of light by the precipitate. The use of the dip probe also makes it possible to automate the solubility analysis, as there is no need for a person to be present to watch the testing.

As a matter of good practice, Applicant has found that if the starting compound is available as a pure free acid, base orampholyte (ie not a salt of the compound) it may not be necessary totally dissolve the compound and then precipitate it. The required conditions of a solution that is close to saturation in contact with the solution may be achieved by partially dissolving the compound at a pH where it will be partially ionised and then proceeding directly to the Chasing Equilibrium phase of the assay.

3. Additional Precipitation

In this optional stage, additional aliquots of the same titrant as used in the Seeking Precipitation stage are added and the pH of the test solution is recorded until the pH has changed by a further pre-defined increment (e.g. 0.5 pH units), or until a fixed time has elapsed (e.g. 60 seconds). The purpose of the Additional Precipitation stage is to ensure that sufficient precipitation is present for the next stage of the method.

4. Chasing Equilibrium

The endpoint of the assay is determined in the Chasing Equilibrium stage, which is the core part of the method of the present invention. In this stage aliquots of acid or base titrant are added to supersaturated or subsaturated test solutions to force them to approach or deviate from equilibrium.

In the Chasing Equilibrium stage the pH of the test solution is measured at regular intervals until a consistent rate of pH change is obtained. A known aliquot of base or acid titrant is added to the test solution to adjust the pH slope, and the slope of this rate of pH change is then measured until a consistent rate of change is again determined. These steps are repeated until the measured pH slope changes sign (i.e. from positive slope to negative slope or vice-versa).

The solubility of the compound is determined as the concentration of unionised compound in solution when the measured pH slope is interpolated to zero. Such determination generally requires plotting a graph of concentration of unionised compound in solution (calculated by reference to known characteristics of the compound and test solution) against pH slope, and the use of interpolation to identify the zero pH slope value.

The steps of the Chasing Equilibrium stage are suitably repeated at least once, preferably from 2 to 8 times, sufficient to give enough data points for confidence in the calculation of solubility of the compound. It will be appreciated that if in a first iteration base is added to the test solution to cause the required change of sign of pH slope, then acid must typically be added in the second iteration (and vice-versa). Each time the slope changes sign, the solubility of the compound can be determined. Multiple changes of the slope are typically made in order to provide multiple measurements of the solubility.

Fuller details of the pH response behaviour during the Chasing Equilibrium stage and of the solubility calculation are provided hereinafter.

As a matter of good practice, the Applicant has found that while chasing equilibrium, it is useful to keep the pH changes small. The acid and base titrants normally used are highly concentrated (0.5 M) and these can cause large changes to the pH of the solution when there is no buffering in the system. These large pH changes are undesirable as they can lead to large changes in the ionisation of the compound and increase the amount of possible error in the final result.

If the titration is taking place at a pH above about 9 or below about 5 then sufficient buffering can be expected to be provided by the water. Moderately soluble compounds will usually precipitate near the pKa of the compound and so the titration then takes place near the pKa and the pKa of the compound provides the necessary buffering.

With highly insoluble compounds the compound may precipitate when the pH is still far from the pKa. If this is also at a pH within a few units of pH 7 then there may be insufficient buffering to closely control the pH using the concentrated titrants. In these case it may be useful to add an quantity of weak acid or base with a pKa near the expected precipitation pH to act as a buffer. As this will usually be used in conjunction with highly insoluble compounds it is important to avoid problems with salt precipitation so only an acidic buffer should be used with an acidic compound and only a basic buffer should be used with a basic compound.

5. Re-Dissolution

This stage occurs after sufficient data has been collected to calculate a solubility value in accord with the method herein. In the Re-Dissolution stage, the pH of the test solution is adjusted to a value at which the ionisable solute becomes fully ionised, and the solution is held at that pH while the ionisable solute dissolves. The purpose of this stage is to ensure that no crystals or solid sample remains on the apparatus that may impair its performance in future assays. After Re-Dissolution, the probes are washed before any further actions take place.

The method herein is suitable for use in a fully automated laboratory apparatus set up operating under the control of a suitably programmed computer.

According to a further aspect of the present invention there is provided a computer program product for use with analytical laboratory apparatus comprising a digital computer comprising software code portions for performing, or requesting user input enabling the performing, of the software implementable steps of the method described above, when said program is run on said digital computer.

BRIEF DESCRIPTION OF THE DRAWINGS

The invention will now be described further with reference to the accompanying drawings, in which.

Figure 1:
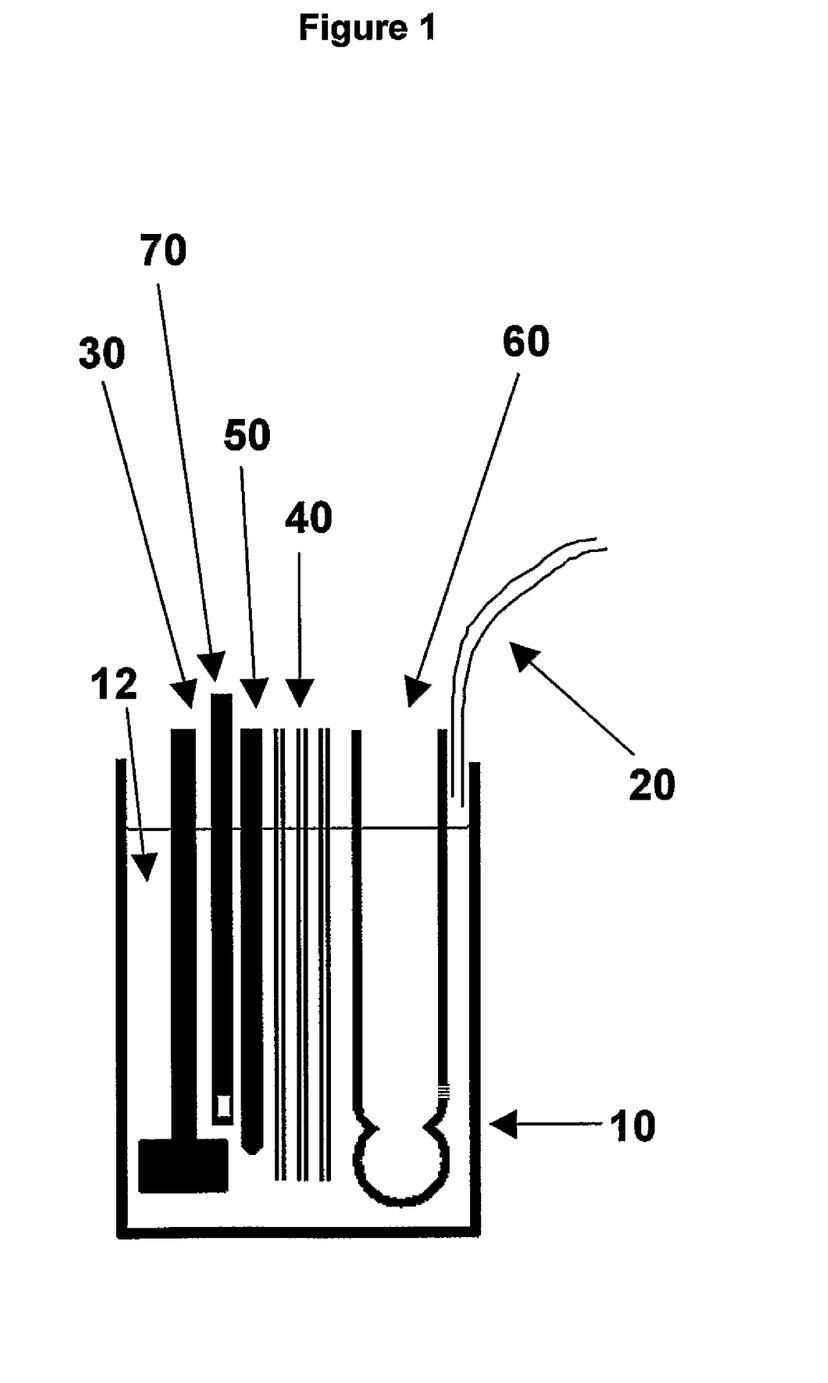
FIG. 1 shows titration apparatus for use in accord with the method of the present invention.

Referring now to the drawings, FIG. 1 illustrates apparatus suitable for use in determining the solubility of a chemical compound by the method herein. Titration vessel 10 is arranged to receive the test sample 12. The titration vessel 10 is placed in an atmosphere of inert gas such as argon supplied via tube 20. The purpose of the inert gas is to exclude atmospheric carbon dioxide. Suitably, the inert gas is constantly replenished to exclude any evolved carbon dioxide gas.

Stirrer 30 connects to a motor (not shown) whose speed of rotation is controlled by a computer program. Dispenser tips 40 are made from narrow tubes and connect to pumps (not shown) that are capable of delivering small, reproducible aliquots of liquid of known volume. The pumps act under the control of a computer program. Temperature sensor 50 connects to a device for measuring temperature. A pH electrode 60 connects to a device for measuring pH, and is calibrated to ensure that pH readings are correct. Spectroscopic dip probe 70 connects via a bundle of optical fibres (not shown) to a device for generating light and to a spectrophotometer (not shown).

Figure 2:
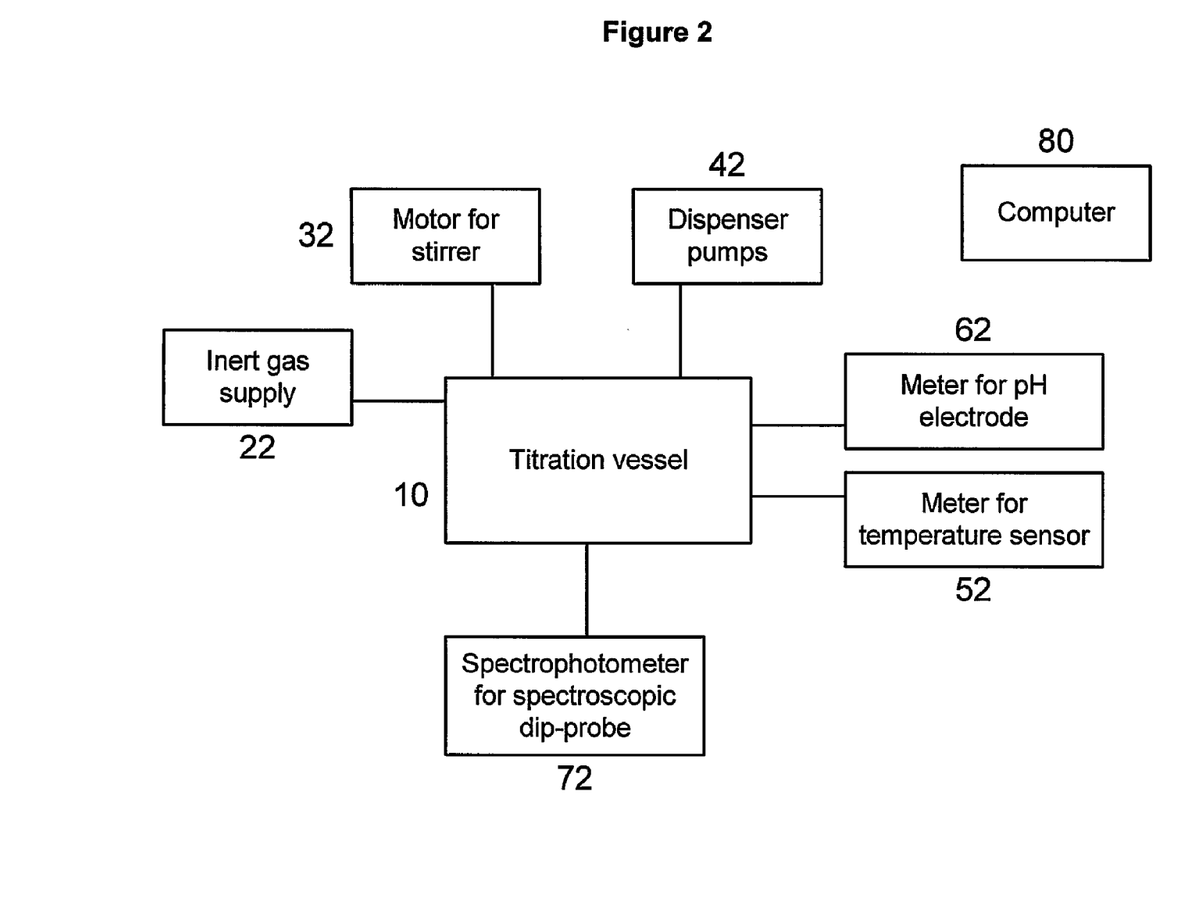
FIG. 2 shows the titration apparatus of FIG. 1 as installed in a representative laboratory set up.

FIG. 2 shows the apparatus of FIG. 1 as connected up to necessary inputs in a laboratory set up.

As shown in FIG. 2, tube 20 connects to an inert gas supply 22 to create an inert gas atmosphere in the environment of the titration vessel 10. Stirrer motor 32 connects to stirrer 30 for drivable rotation thereof. Pumps 42 connect to dispenser tips 40 for the supply of delivering small, reproducible aliquots of liquid of known volume thereto. Device for measuring temperature 52 connects to temperature sensor 50. Suitably calibrated device for measuring pH 62 connects to pH electrode 60. Spectrophotometer and device for generating light 72 connects to spectroscopic dip probe 70 via a bundle of optical fibres. The whole set up is arranged for automation under the control of computer 80 that connects to motor 32, pumps 42, temperature measuring device 52, pH meter 62 and spectrophotometer 72.

The method herein is illustrated by reference to a solubility determination on the pharmaceutical compound, diclofenac. Diclofenac is a carboxylic acid with molecular weight of 296.1 for the free acid.

A hyperconcentrated test solution of the sodium salt of diclofenac with a formula weight of 318.1 was initially prepared by weighing 0.00556 grams, and adding 10 mL of 0.15M KCl solution.

Dissolution, Seeking Precipitation and Additional Precipitation

Figure 3:
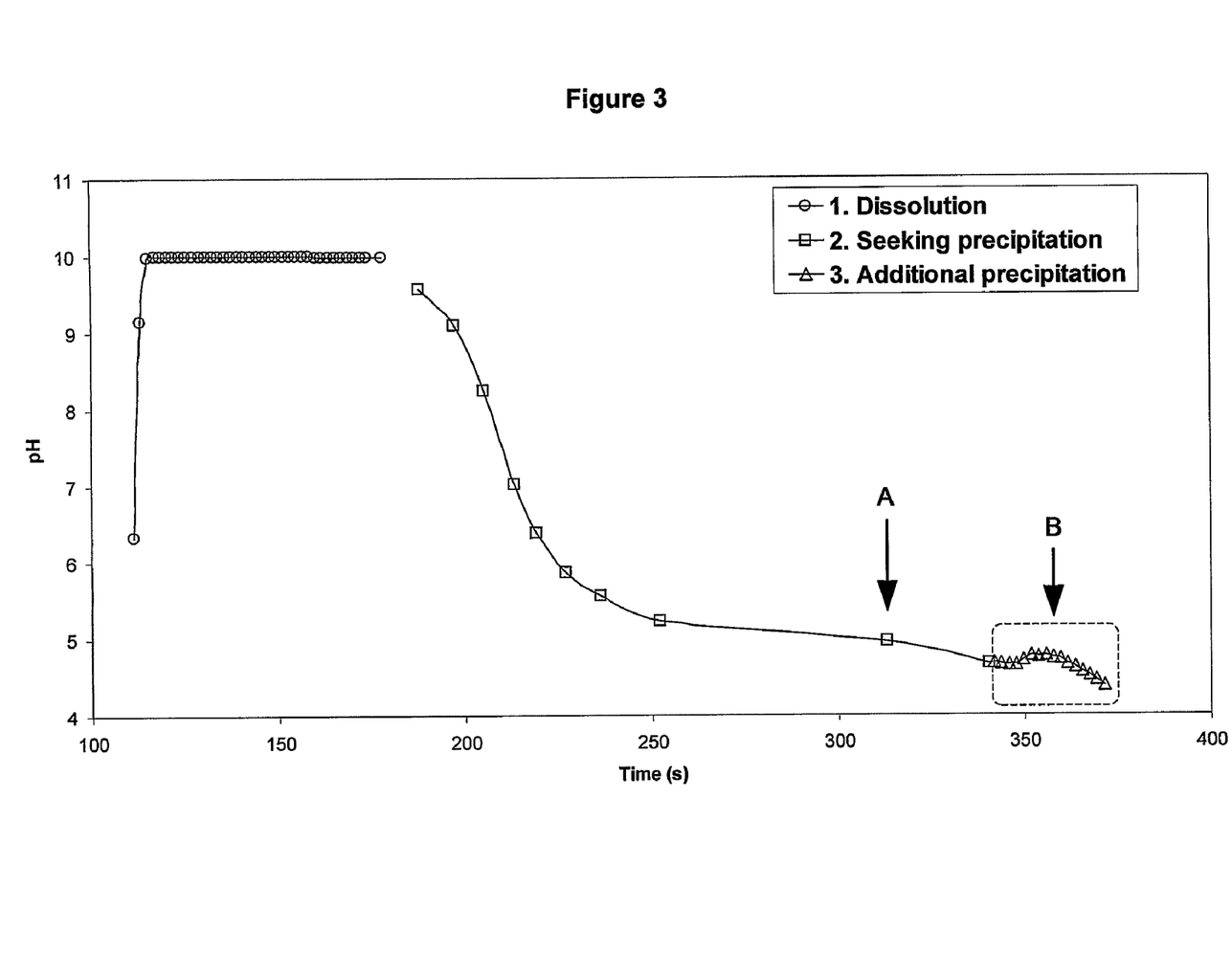
FIG. 3 shows a graph of pH versus Time (seconds) for a test solution in the Dissolution, Seeking Precipitation and Additional precipitation stages of a suitable method herein.

The Dissolution, Seeking Precipitation and Additional Precipitation stages of the method are as conducted on the diclofenac test solution are illustrated in FIG. 3.

In the Dissolution stage, the test solution is titrated with base titrant. In the Seeking Precipitation and Additional Precipitation stages, the test solution is titrated with acid titrant.

While unionised solute is precipitating from a supersaturated solution of an acid such as diclofenac, the pH goes up if no titrant is added because the concentration of unionised species $AH_{aq}$ in solution decreases. If acid titrant is added while the unionised solute is precipitating, the pH can be forced to go down, as shown in the Additional Precipitation stage.

Chasing Equilibrium

After the final data point of the Additional Precipitation stage has been collected, the method moves on to the Chasing Equilibrium stage. Chasing Equilibrium for an acidic sample is based on the following principles:

After precipitation of the unionised species has occurred, the ionisable solute can be in one of three possible states.

1. The solution may be supersaturated, and the dissolved unionised species $AH_{aq}$ is precipitating. If no titrant is added, and if the solutions do not contain dissolved carbonate or carbon dioxide, the pH will go up until the solution reaches equilibrium.

2. The solution may be subsaturated, the precipitated unionised species $AH_{solid}$ is dissolving. If no titrant is added, and if the solutions do not contain dissolved carbonate or carbon dioxide, the pH will go down until the solution reaches equilibrium.

3. The solution may be at equilibrium.

While it is theoretically possible to determine the pH at equilibrium from cases 1 or 2 above, it is difficult in practice for two reasons—it would be necessary to wait a very long time (e.g. several hours) for solutions to reach full equilibrium, and it is very difficult to exclude carbon dioxide and carbonate from the titration vessel.

Carbon dioxide is readily absorbed from the air by aqueous solutions, to form a solution of carbonic acid. The rate of absorption and desorption, and therefore the concentration of carbon dioxide changes with pH; the degree of protonation of carbonic acid also changes with pH. In consequence, the measured pH of all aqueous solutions exposed to the air is affected by carbon dioxide, in a way that is difficult to predict.

Thus in accord with the present invention, the Chasing Equilibrium is employed in which, aliquots of acid or base titrant are added to supersaturated or subsaturated solutions to force them to approach or deviate from equilibrium. The presence of carbon dioxide is minimised by working in an inert atmosphere, though it is difficult to remove it completely.

The pH Response while Chasing Equilibrium

To understand Chasing Equilibrium, it is first necessary to examine the response of the pH electrode when acid or base is added to a solution containing a precipitate of ionisable solute. Three examples will be considered. In each example, the pH electrode displays three types of response—a short-term response, a multi-variate response, and a sustained response.

(a) Adding Base Titrant to a Supersaturated Solution of Unionised Acid

Figure 4:
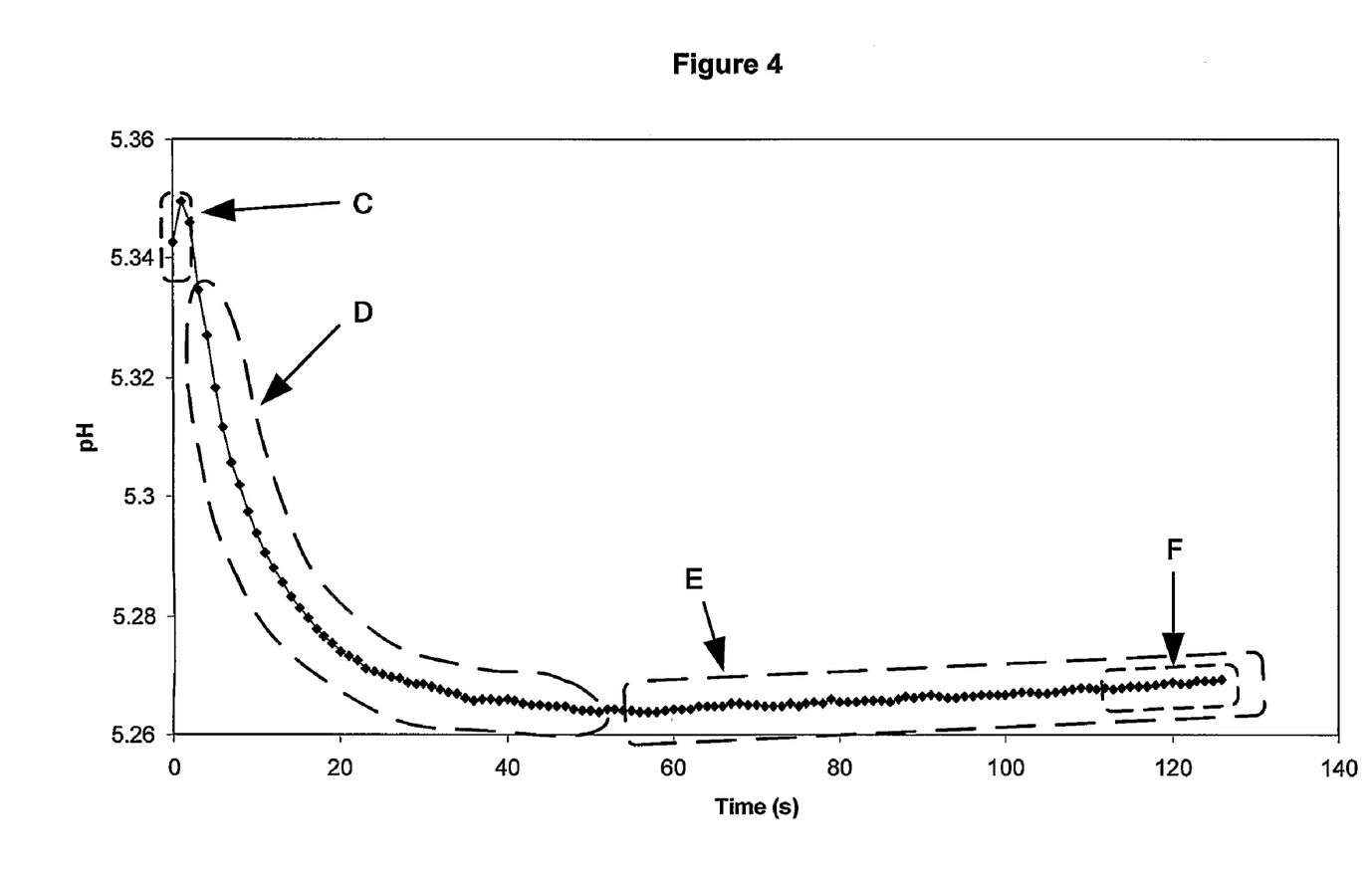
FIG. 4 shows a graph of pH versus Time (seconds) for a test solution in one aspect of a Chasing Equilibrium stage of a suitable method herein, in which base titrant is added to a supersaturated solution of unionised acid test compound.

An aliquot of base titrant is added at Time=0 in FIG. 4, and pH is measured and recorded at regular time intervals (e.g. once per second) until the change in pH has reached a settled direction and a stable rate.

In more detail, FIG. 4 illustrates the pH response curve showing pH measured at regular time intervals (e.g. every second) after base titrant has been added to a supersaturated solution in which the unionised sample is precipitating.

In FIG. 4, it may be seen that the pH electrode responds to several different properties of the solution. In Section 1 of the curve, it is shown responding to the free base titrant added to the solution. Soon the free base titrant begins to react with dissolved solute. In Section 2 the pH electrode shows a multi-variate response, governed by ionisation of the dissolved solute, the precipitation of the solute, the absorption/desorption of carbon dioxide, the protonation/deprotonation of carbonic acid and the response time of the pH electrode. The reactions governing Section 1 and Section 2 reach a steady state after about 60 seconds. In Section 3, the pH electrode responds predominantly to the increase in pH that occurs as the sample precipitates. When the linear fit of a number of the final pH points (e.g. 15 points) of this sustained response curve is better than a requested value (e.g. $r^2=0.95$), the final pH and the slope of the line are recorded.

(b) Adding Base Titrant to a Subsaturated Solution of Unionised Acid

Figure 5:
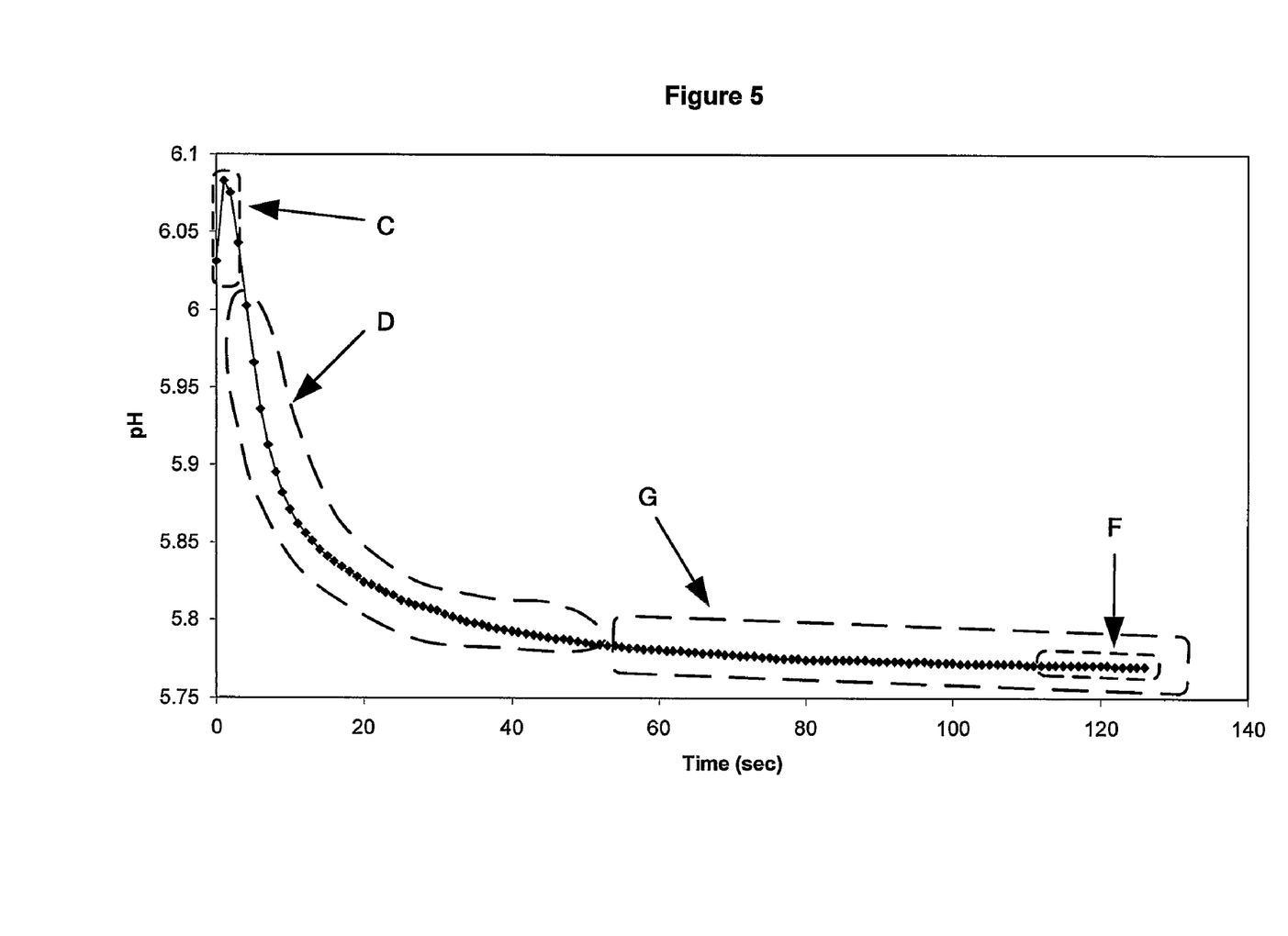
FIG. 5 shows a graph of pH versus Time (seconds) for a test solution in another aspect of a Chasing Equilibrium stage of a suitable method herein, in which base titrant is added to a subsaturated solution of unionised acid test compound.

An aliquot of base titrant is added at Time=0 in FIG. 5, and pH is measured and recorded at regular time intervals (e.g. once per second) until the change in pH has reached a settled direction and a stable rate.

In more detail, FIG. 5 illustrates the pH response curve showing pH measured at regular time intervals (e.g. every second) after base titrant has been added to a subsaturated solution in which the unionised sample is dissolving.

In FIG. 5, the pH electrode responds to several different properties of the solution. In Section 1 of the curve, it is shown responding to the free base titrant added to the solution. Soon the free base titrant begins to react with dissolved solute. In Section 2 the pH electrode shows a multi-variate response, governed by ionisation of the dissolved solute, the dissolution of the solute, the absorption/desorption of carbon dioxide, the protonation/deprotonation of carbonic acid and the response time of the pH electrode. The reactions governing Section 1 and Section 2 reach a steady state after about 60 seconds. In Section 3, the pH electrode responds predominantly to the decrease in pH that occurs as the sample dissolves. When the linear fit of a number of the final pH points (e.g. 15 points) of this sustained response, curve is better than a requested value (e.g. $r^2=0.95$), the final pH and the slope of the line are recorded.

(c) Adding Acid Titrant to a Supersaturated Solution of Unionised Acid

Figure 6:
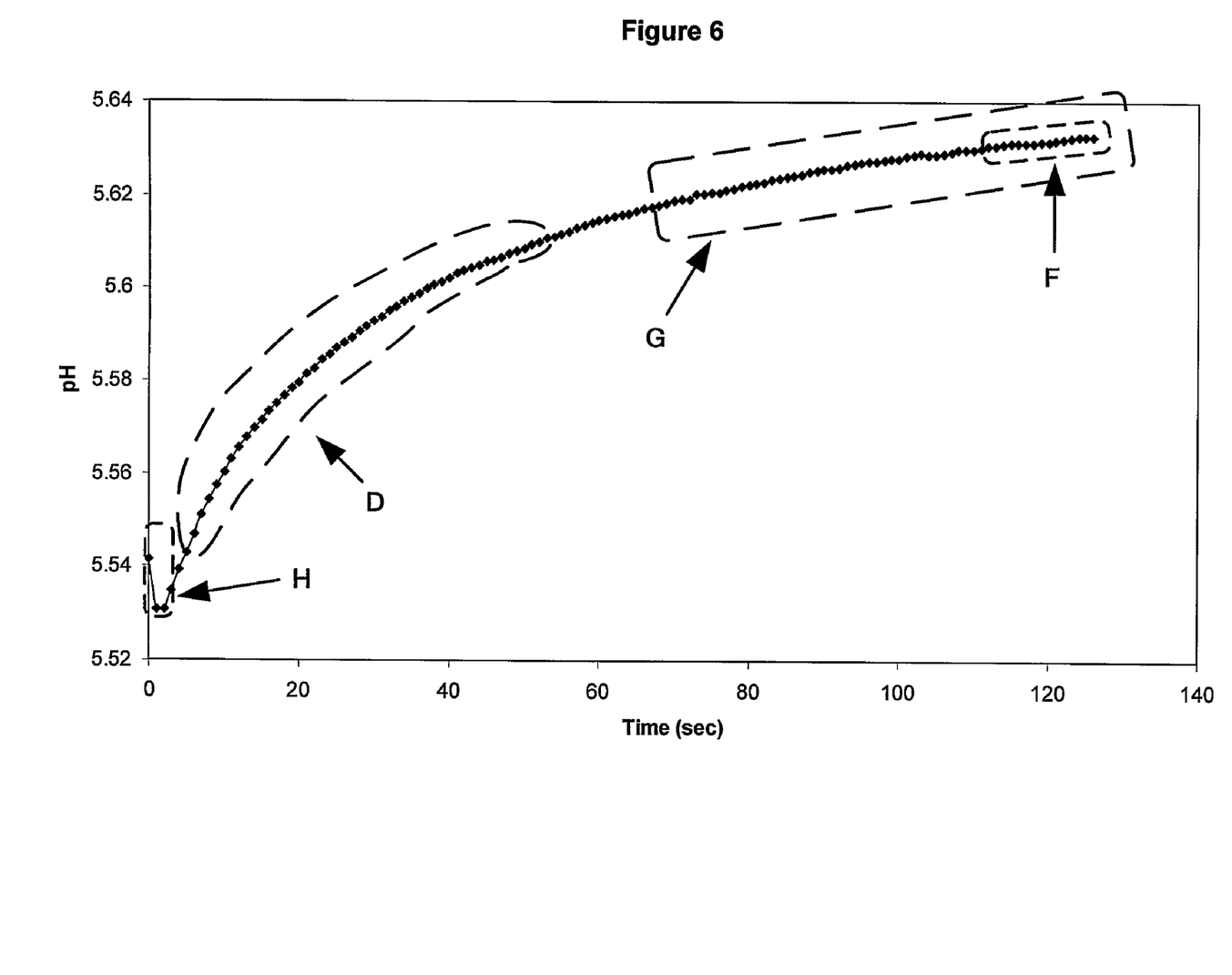
FIG. 6 shows a graph of pH versus Time (seconds) for a test solution in one aspect of a Chasing Equilibrium stage of a suitable method herein, in which acid titrant is added to a supersaturated solution of unionised acid test compound.

An aliquot of acid titrant is added at Time=0 in FIG. 6, and pH is measured and recorded at regular time intervals (e.g. once per second) until the change in pH has reached a settled direction and a stable rate.

In more detail, FIG. 6 illustrates the pH response curve showing pH measured at regular time intervals (e.g. every second) after acid titrant has been added to a supersaturated solution in which the unionised sample is precipitating.

In FIG. 6, the pH electrode responds to several different properties of the solution. In Section 1 of the curve, it is shown responding to the free acid titrant added to the solution. Soon the free acid titrant begins to react with dissolved solute. In Section 2 the pH electrode shows a multi-variate response, governed by ionisation of the dissolved solute, the precipitation of the solute, the absorption/desorption of carbon dioxide, the protonation/deprotonation of carbonic acid and the response time of the pH electrode. The reactions governing Section 1 and Section 2 reach a steady state after about 60 seconds. In Section 3, the pH electrode responds predominantly to the increase in pH that occurs as the sample precipitates. When the linear fit of a number of the final pH points (e.g. 15 points) of this sustained response curve is better than a requested value (e.g. $r^2$=0.95), the final pH and the slope of the line are recorded.

Monitoring while Chasing Equilibrium

Figure 7:
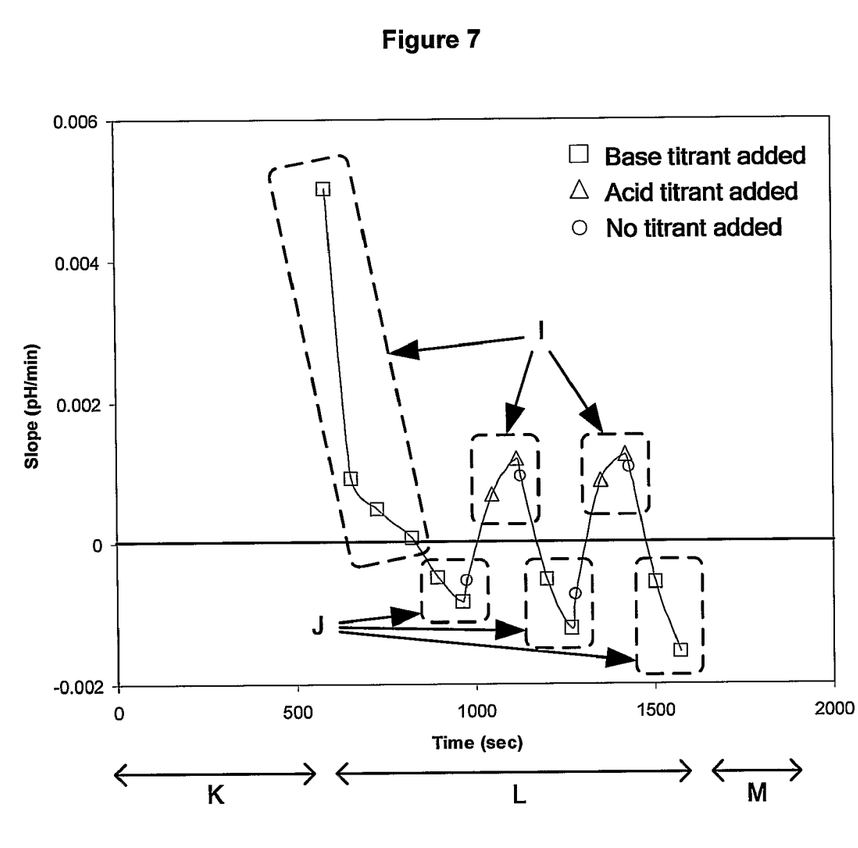
FIG. 7 shows a graph of pH slope (pH/min) versus Time for a test solution during the Chasing Equilibrium stage of a suitable method herein.

FIG. 7 illustrates monitoring of the progress of Chasing Equilibrium. The slope (pH/min) of the sustained pH electrode response is plotted against time (seconds).

The first points are collected while adding base titrant to a supersaturated test solution. The addition of titrant is controlled by a computer program. The slope decreases with each aliquot of base that is added. Eventually the slope changes sign, indicating that the solution has become subsaturated. Another aliquot of base is added to confirm that the slope is negative. If the slope remains negative, another data point is taken after adding no titrant. Aliquots of acid are then added until the slope becomes positive, indicating that the solution has become supersaturated again. By successively adding aliquots of base and acid, the slope can be forced to change direction. When the slope has changed direction several (e.g. five) times the Chasing Equilibrium stage of the procedure is deemed to be complete.

Re-Dissolution of the ionisable solute is then implemented. This is achieved by adjusting the pH of the test solution to a value at which the ionisable solute becomes fully ionised, and the solution is held at that pH while the ionisable solute dissolves.

The purpose of Re-Dissolution is to ensure that no crystals or solid sample remains on the apparatus that may impair its performance in future assays. The various probes are washed before any further actions take place.

Determining the Solubility of the Test Compound.

Figure 8:
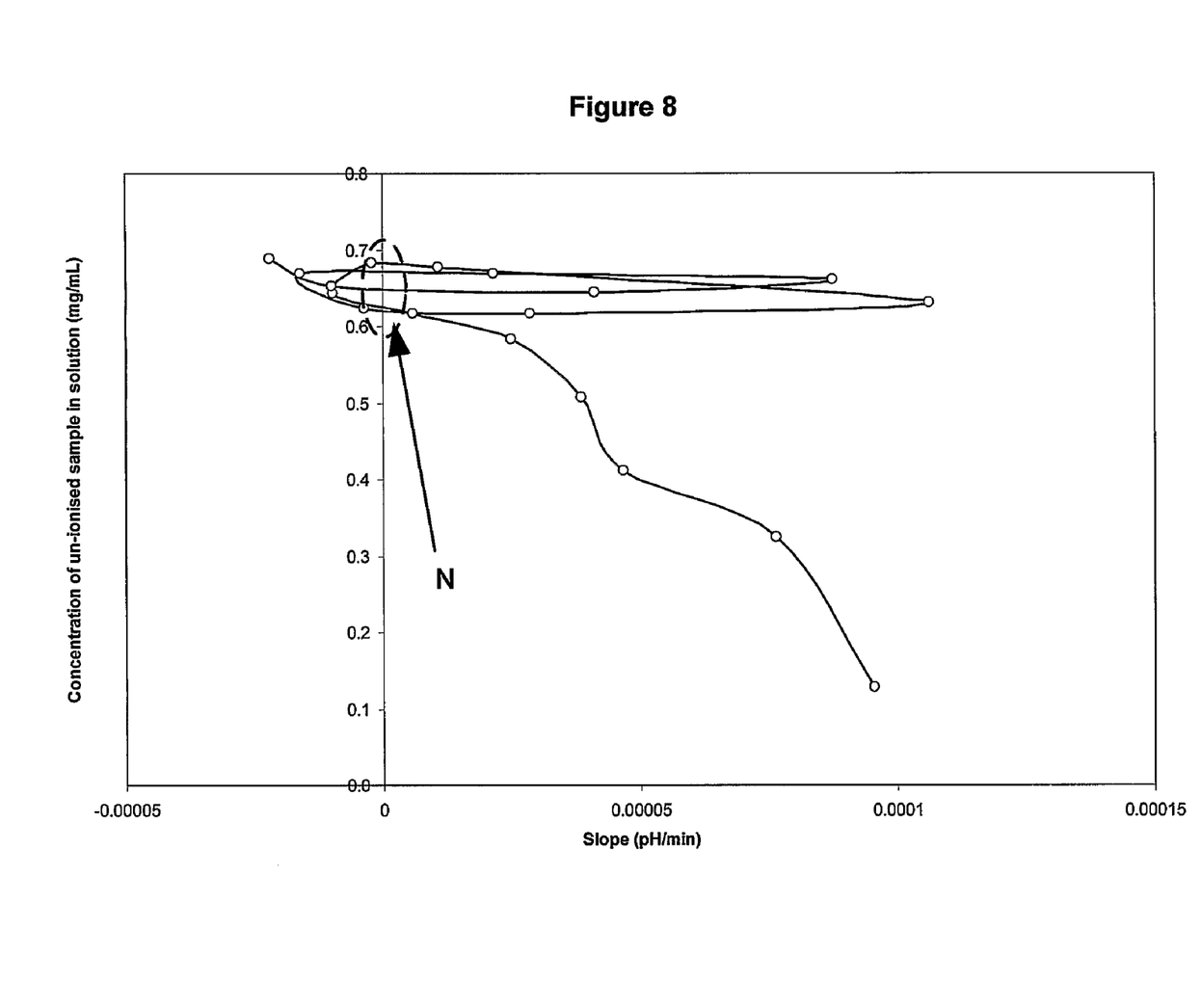
FIG. 8 shows a graph of concentration of unionised test compound in solution (μg/mL) versus pH slope (pH/min) for a test solution during a Chasing Equilibrium stage of a suitable method herein.

The concentration of unionised solute in solution is calculated for each point in FIG. 7, and plotted against slope (pH/min) as shown in FIG. 8. The points are then connected by a line in the same order that they appeared in FIG. 7. The points corresponding to where the line crosses the zero value of the slope (pH/min) axis are determined by interpolation. The concentration equivalent to these zero slope, crossing points is determined. The solubility is then obtainable as the mean concentration calculated from the several zero slope, crossing points.

Calculating the Solubility Value of the Test Compound

Before the method is conducted, the following are known:
(i) The molecular weight of the sample.
(ii) The formula weight of the sample, which is different from the molecular weight if the sample is introduced as a salt.
(iii) The weight of sample added.
(iv) The concentration of the acid and base titrants.
(v) The acidity constant ($pK_a$) of the test compound.

At each point the volume of added water, acid and base titrant is known and the pH obtained by measurement.

For each point located on either side of a zero slope crossing, the amount of neutral sample in solution could be calculated in the following steps:

1. The total volume of the assay is the sum of water, acid and base titrants that have been added.

$$v_t = v_w + v_a + v_b$$

2. The concentration of free hydrogen ions is:

$$[H^+] = 10^{-pH}$$

3. The concentration of free hydroxide ions is:

$$[OH^-] = K_w/[H^+]$$

wherein: $K_w$ is the acidity constant of water (i.e. $10^{-14}$).

4. The concentration of free positive ions (e.g. $K^+$) is determined from the amount of base titrant (e.g. KOH) plus any positive ions in the test compound if it was a salt:

$$[K^+] = (v_b c_b + m_s z_{s+}/w_f)/v_t$$

wherein: $c_b$ is the concentration of base titrant
$m_s$ is the sample weight of test compound
$z_{s+}$ is the charge of any positive salt counter-ions
$w_f$ is the formula weight of the test compound.

5. The concentration of free negative ions (e.g. $Cl^-$) is determined from the amount of acid titrant (e.g. HCl) plus any negative ions in the original sample if it was a salt:

$$[Cl^-] = (v_a c_a + m_s z_{s-}/w_f)/v_t$$

wherein: $c_a$ is the concentration of acid titrant
$m_s$ is the sample weight of test compound
$z_{s-}$ is the charge of any negative salt counter-ions
$w_f$ is the formula weight of the test compound.

6. The concentration of ionised sample can now be determined from a charge balance equation. For a monoprotic acid like diclofenac, for example, this is simply the concentration of the deprotonated species:

$$[X^-] = [H^+] - [OH^-] + [K^+] - [Cl^-]$$

7. From the known pH and ionisation constant ($pK_a$), the amount of neutral species in solution can be determined:

$$[X] = [H^+][X^-]/K_a$$

In variations of the above calculation steps, a number of other factors would normally be taken into account (such as temperature, ionic strength and carbonate) to make the calculations more accurate, but the same basic steps would be followed.

Example Calculation for Diclofenac

These values are known at the start of the test assay and are constant throughout the assay:
$pK_w$=14, $K_w$=1.00 E−14
$pK_a$=3.98, $K_a$=1.05 E−4
sample weight $m_s$=5.56 mg
formula weight $w_f$=318.1 g/mole
molecular weight $w_m$=296.1 g/mole
base concentration $c_b$=0.1 M/kg
acid concentration $c_a$=0.1 M/kg Point A Measured Values At a first point ('point A') one side of a zero-slope crossing point, the measured values are as follows:
water volume $v_w$=10.00000 ml
acid volume $v_a$=0.19291 ml
base volume $v_b$=0.03000 ml
pH=5.64453
pH slope=2.87 E−05
Thus, the calculated values are as follows:
total volume $v_t$=10.22291 ml
$[H^+]$=2.267 E−06 M
$[OH^-]$=4.411 E−09 M
$[K^+]$=2.003 E−03 M
$[Cl^-]$=1.887 E−03 M
$[X^-]$=1.185 E−04 M
$[HX]$=2.565 E−06 M
This gives a value for dissolved neutral test sample of 759 ng/ml.

Point B Measured Values

At a second point ('point B') the other side of a zero-slope crossing point, the measured values are as follows:
- water volume $v_w$=10.00000 ml
- acid volume $v_a$=0.19291 ml
- base volume $v_b$=0.03125 ml
- pH=5.70437
- pH slope=−3.5 E−06

Thus, the calculated values are as follows:
- total volume $v_t$=10.22416 ml
- [$H^+$]=1.975 E−06 M
- [$OH^-$]=5.063 E−09 M
- [$K^+$]=2.015 E−03 M
- [$Cl^-$]=1.887 E−03 M
- [$X^-$]=1.304 E−04 M
- [HX]=2.459 E−06 M This gives a value for dissolved neutral test sample of 728 ng/ml.

Figure 9:
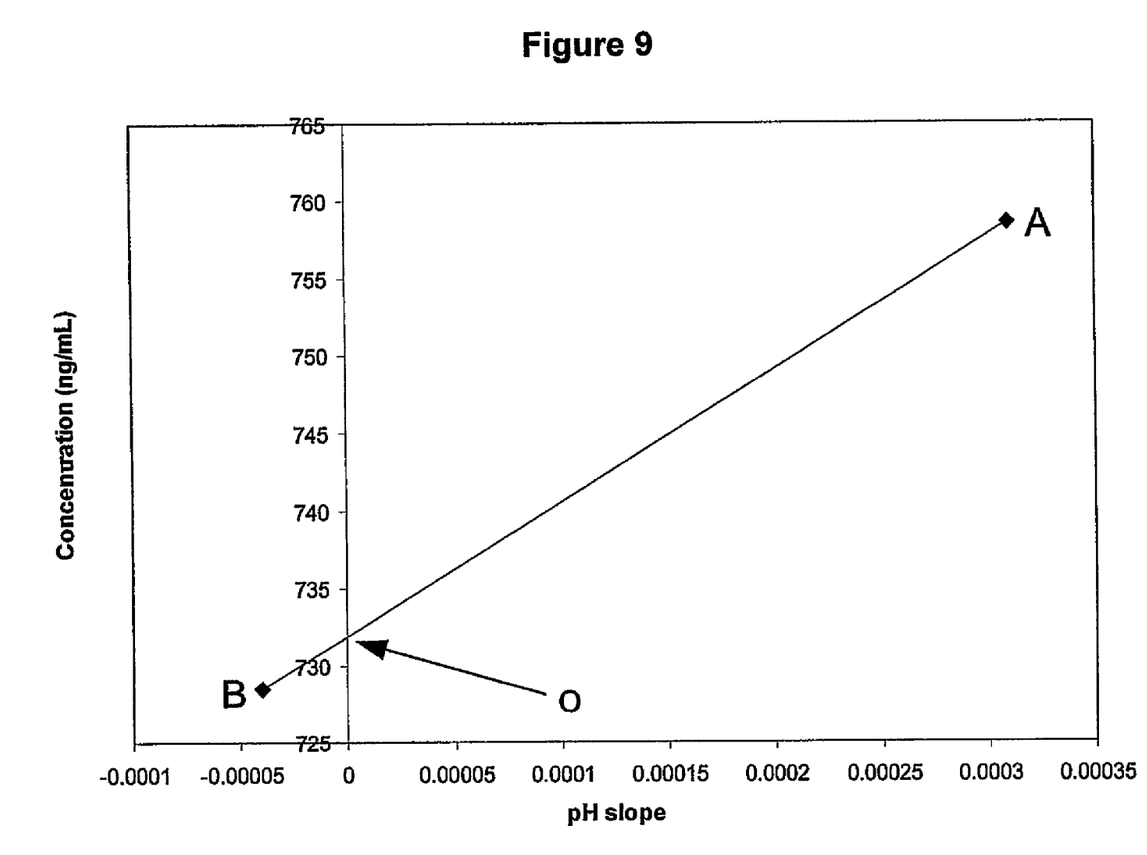
FIG. 9 shows a graph of calculated concentration of dissolved test compound versus pH slope (pH/min) in a test solution obtained by way of a suitable method herein.

Straight line interpolation of the two points A and B to a zero slope gives an answer for the equilibrium solubility of diclofenac of around 732 ng/ml. FIG. 9 shows a subset of FIG. 8, highlighting the crossing point for the two points in this example.

Applicant has also found that additional calculations may be formed using the data collected by the described method. Thus, the precipitation rate and/or dissolution rate may be determined from the pH slope. In other aspects, the pH slope during precipitation and/or dissolution may be used to determine the solubility of the compound.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

Labelling of Figures

In FIGS. 3 to 9, the following labelling applies:
A Precipitation first observed here
B pH forced to go down by adding acid
C 1. Short term response to the free base titrant. This small, steep curve is sometimes swamped by the next.
D 2. Multi-variate response typically 60 seconds.
E 3. Sustained response to the precipitation of AH ($AH_{aq}$→$AH_{solid}$), and to changes in the carbonate concentration.
F The slope of this line is reported when a consistent slope is detected.
G 3. Sustained response to the dissolution of AH ($AH_{solid}$→$AH_{aq}$), and to changes in the carbonate concentration.
H 1. Short term response to the free acid titrant. This small, steep curve is sometimes swamped by the next.
I Solution is supersaturated, neutral species is precipitating.
J Solution is subsaturated, neutral species is dissolving
K Dissolution, seeking precipitation and additional precipitation
L Chasing equilibrium
M End
N Solubility is equivalent to the mean value of the points where the graph line crosses the zero slope line
O Crosses zero slope at 732 ng/ml

The invention claimed is:

1. A method of determining the solubility of a chemical compound containing one or more acidic or basic groups comprising:
    (a) preparing a close to saturated solution of said chemical compound with solid of the chemical compound present;
    (b) measuring and recording the pH of the test solution at regular time intervals until a consistent rate of pH change is obtained, and measuring the slope of said consistent rate of pH change with time;
    (c) subsequently adding an aliquot of base or acid titrant of known concentration to the test solution to adjust the pH slope;
    (d) repeating steps (b) and (c) until the measured pH slope changes from a positively-signed pH slope to a negatively-signed pH slope, or vice-versa;
    (e) determining the concentration of unionised compound in a said test solution when said consistent rates of pH change were obtained, and
    (f) determining the solubility of the compound as the concentration of unionised compound in solution when the measured pH slope is interpolated to be zero on a graph of concentration of said unionised compound versus pH slope.

2. A method according to claim 1, wherein step (a) comprises the steps of:
    (i) providing a known volume of water and a known amount of said compound to a titration vessel to form a test solution;
    (ii) optionally, adding a volume of base or acid titrant to said test solution sufficient to adjust the pH thereof to fully dissolve the compound in ionised form, thereby creating a hyperconcentrated solution;
    (iii) adding one or more known aliquots of acid or base titrant to the test solution until the unionised compound begins to precipitate out of the test solution;
    (iv) optionally, adding one or more additional known aliquots of acid or base titrant to the test solution to cause additional precipitation of the unionised compound out of the test solution.

3. A method according to claim 2, wherein the chemical compound contains one or more acidic groups and step (a) comprises the steps of:
    (i) providing a known volume of water and a known amount of said compound to a titration vessel to form a test solution;
    (ii) optionally, adding a volume of base titrant to said test solution sufficient to adjust the pH thereof to fully dissolve the compound in ionised form, thereby creating a hyperconcentrated solution;
    (iii) adding one or more known aliquots of acid titrant to the test solution until the unionised compound begins to precipitate out of the test solution;
    (iv) optionally, adding one or more additional known aliquots of acid titrant to the test solution to cause additional precipitation of the unionised compound out of the test solution.

4. A method according to claim 2, wherein the chemical compound contains one or more basic groups and step (a) comprises the steps of:
    (i) providing a known volume of water and a known amount of said compound to a titration vessel to form a test solution;
    (ii) optionally, adding a volume of acid titrant to said test solution sufficient to adjust the pH thereof to fully dissolve the compound in ionised form, thereby creating a hyperconcentrated solution;

(iii) adding one or more known aliquots of base titrant to the test solution until the unionised compound begins to precipitate out of the test solution;

(iv) optionally, adding one or more additional known aliquots of base titrant to the test solution to cause additional precipitation of the unionised compound out of the test solution.

5. A method according to claim 1, wherein the chemical compound is a pharmaceutical or agrochemical chemical compound.

6. A method according to claim 1, wherein the chemical compound has a solubility of from 100 ng/ml to 30 mg/ml.

7. A method according to claim 1, wherein precipitation of the chemical compound is detectable by a visual or spectroscopic method.

8. A method according to claim 1, wherein step (d) is repeated from one to eight times.

9. A method according to claim 1, wherein the test solution is mixed throughout the method.

10. A method according to claim 1, wherein the pH of the test solution is monitored throughout the method.

11. A method according to claim 1, additionally comprising the step (g) adjusting the pH of the test solution to a value at which the chemical compound dissolves and holding the pH to at least that value until the chemical compound fully dissolves.

12. A method according to claim 1, additionally comprising supplying the titration vessel with an inert gas to provide an inert testing environment.

13. A method according to claim 1, wherein a co-solvent is provided to the test solution.

14. A computer program product for use with analytical laboratory apparatus comprising a digital computer comprising software code portions for performing, or requesting user input enabling the performing, of the software implementable steps of the method according to claim 1, when said program is run on said digital computer.

* * * * *